(12) United States Patent
Greig et al.

(10) Patent No.: US 9,993,141 B2
(45) Date of Patent: Jun. 12, 2018

(54) CONTROL SYSTEM FOR MEDICAL DEVICES AND RELATED METHODS OF USE

(71) Applicant: Boston Scientific Scimed, Inc., Maple Grove, MN (US)

(72) Inventors: Robinson Greig, Tivoli, NY (US); Jeffrey Bean, Fitchburg, MA (US); Kevin Zephir, Westminster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days. days.

(21) Appl. No.: 15/265,188

(22) Filed: Sep. 14, 2016

(65) Prior Publication Data

US 2017/0000313 A1    Jan. 5, 2017

Related U.S. Application Data

(63) Continuation of application No. 14/196,660, filed on Mar. 4, 2014, now Pat. No. 9,462,931, which is a continuation of application No. 61/772,615, filed on Mar. 5, 2013.

(51) Int. Cl.
| | |
|---|---|
| *A61B 1/00* | (2006.01) |
| *A61B 1/005* | (2006.01) |
| *A61M 25/01* | (2006.01) |
| *A61B 17/00* | (2006.01) |

(52) U.S. Cl.
CPC ........ *A61B 1/0052* (2013.01); *A61B 1/00039* (2013.01); *A61B 1/0057* (2013.01); *A61M 25/0136* (2013.01); *A61B 2017/00327* (2013.01); *A61M 2025/015* (2013.01)

(58) Field of Classification Search
USPC ..... 600/146–147, 149–150; 474/47–57, 185; 248/232, 332, 572
See application file for complete search history.

(56) References Cited

U.S. PATENT DOCUMENTS

| | | | |
|---|---|---|---|
| 4,941,455 A | 7/1990 | Watanabe | |
| 5,667,476 A * | 9/1997 | Frassica | A61B 1/0052 600/139 |
| 8,137,308 B2 * | 3/2012 | Schultz | A61M 25/0136 600/434 |
| 8,808,166 B2 | 8/2014 | Hosaka | |
| 8,974,376 B2 | 3/2015 | Okamoto | |
| 2002/0143238 A1 | 10/2002 | Hino | |
| 2003/0092965 A1 | 5/2003 | Konomura | |
| 2008/0275302 A1 | 11/2008 | Hosaka | |
| 2009/0137353 A1 | 5/2009 | Serkh | |
| 2013/0060088 A1 | 3/2013 | Okamoto | |

(Continued)

Primary Examiner — Matthew J Kasztejna
(74) Attorney, Agent, or Firm — Bookoff McAndrews, PLLC (57) ABSTRACT

A system for controlling a medical device includes a shaft rotatable about a longitudinal axis and a plurality of arms extending radially outwards from the shaft. Each arm includes an inward end positioned near the shaft and an outward end. The system also includes a collapsible pulley formed from a plurality of pulley pieces. At least one of the pulley pieces is slidably mounted on at least one of the plurality of arms and has a surface configured to receive at least one control element. The system further includes at least one biasing member located between the shaft and the at least one slidably-mounted pulley piece.

18 Claims, 5 Drawing Sheets

(56) References Cited

U.S. PATENT DOCUMENTS

2013/0331652 A1 12/2013 Okamoto
2013/0338441 A1 12/2013 Okamoto
2016/0073856 A1 3/2016 Saito \* cited by examiner

CONTROL SYSTEM FOR MEDICAL DEVICES AND RELATED METHODS OF USE

CROSS-REFERENCE TO RELATED APPLICATIONS

This application is a continuation application of U.S. application Ser. No. 14/196,660, filed Mar. 4, 2014, which claims the benefit of priority from U.S. Provisional Application No. 61/772,615, filed on Mar. 5, 2013. The entire disclosure of each of the above applications is incorporated herein by reference.

FIELD

This disclosure relates generally to systems and methods for controlling devices. More particularly, an embodiment of the present disclosure relates to a system for steering medical devices, such as, e.g., an endoscope having a deflectable distal end.

BACKGROUND

In general, a medical device may include an elongate portion configured to be inserted into a body cavity, and the elongate portion may be coupled with a control portion. The medical device may also include a steering mechanism, which may be adapted to steer a distal tip of the medical device. The steering mechanism may include steering wires disposed lengthwise through lumens in the elongate portion. The steering wires may attach a distal end of the elongate portion to the control portion. In certain instances, a proximal end of a selected steering wire may be tensioned, which may cause deflection of the distal tip of the medical device in a select direction, such as, for example, left-right or up-down.

In some conventional medical devices, two steering wires may be tensioned using a pulley located in the control portion of the medical device. The pulley may include a pulley wheel mounted on a shaft, and the two steering wires may be connected to the circumference of the pulley wheel. Rotation of the shaft may pull one wire in a proximal direction while releasing the other wire, resulting in deflection of the distal tip of the medical device. In certain embodiments, the force required for rotating the pulley may increase as the wire is pulled farther. Such increased force may interfere with smooth and unencumbered steering of the medical device.

Therefore, a need exists for an improved control system for steering the medical device.

SUMMARY

According to an embodiment, a system for controlling a medical device includes a shaft rotatable about a longitudinal axis and a plurality of arms extending radially outwards from the shaft. Each arm includes an inward end positioned near the shaft and an outward end. The system also includes a collapsible pulley formed from a plurality of pulley pieces. At least one of the pulley pieces is slidably mounted on at least one of the plurality of arms and has a surface configured to receive at least one control element. The system further includes at least one biasing member located between the shaft and the at least one slidably-mounted pulley piece.

According to another embodiment, a medical device includes a control system including a shaft rotatable about a longitudinal axis and a plurality of arms extending radially outwards from the shaft. The plurality of arms includes an inward end positioned near the shaft and an outward end. The control system also includes a collapsible pulley formed from a plurality of pulley pieces mounted on the respective arms, and at least one of the pulley pieces is slidably mounted on at least one of the arms. The control system further includes at least one biasing member located between the shaft and the at least one slidably-mounted pulley piece and at least one control element coupled to one of the pulley pieces. The medical device also includes an end effector coupled to a distal end of the medical device and connected to a distal end of the at least one control element.

According to yet another embodiment, a method for steering a distal end of a medical device includes rotating a shaft of a control system about a longitudinal axis to rotate a collapsible pulley formed from a plurality of pulley pieces mounted on a plurality of arms. The method also includes sliding at least one of the pulley pieces along at least one of the arms, and each arm includes an inward end positioned near the shaft and an outward end positioned away from the shaft. The method further includes compressing at least one biasing member located between the inward end and the outward end, and tensioning at least one control element releasably coupled to at least one of the plurality of pulley pieces.

Additional objects and advantages of the claimed disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate embodiments of the present disclosure and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts.

Embodiments of the present disclosure may relate to systems and methods for steering a medical device, such as an endoscope. As is generally known in the art, an endoscope may include an elongate member having a distal end, a proximal end, and a lumen extending between the distal and proximal ends. The proximal end of the endoscope may include a hub having multiple ports, through which a user may insert an instrument (not shown), such as scissors, forceps, or the like. Further, the instrument may include one or more lumens, which may allow one or more control elements (e.g., steering wires, cables, ribbons, or other elongate structures) to pass therethrough.

A control system or mechanism may be configured to control the movement of the one or more control elements in one or more directions to deflect a distal end of the medical device, such as an end effector, in any suitable direction such as left-right, up-down, or the like. For example, a distal portion of the control element may attach to the end effector, and a proximal portion of the control element may be attached to a handle having a knob, lever, button, or other movable element. When a user activates the handle, such as by turning the knob, the control element may be pulled in a proximal direction, which may result in displacement of the distal end of the medical device back and forth or in other directions, such as up and down. This turning of the knob may steer or operate the end effector.

A control system may be configured to pull the control element using at least one collapsible pulley having a variable effective diameter. The system may also include a knob at the handle that may rotate the collapsible pulley and thereby pull the control element to deflect the distal end. There may be a direct relation between the force applied on the knob and a torque produced in the pulley to steer the distal end. An increasing resistance to movement may cause the pulley to collapse, and the effective pulley diameter may decrease. The decrease in effective pulley diameter may provide an increase in gear ratio between the knob and the pulley. The gear ratio may be indicated by a ratio of the diameter of the knob (or other device that is rotated to cause the rotation of the pulley) to the effective diameter of the pulley. The increased gear ratio thus may provide a mechanical advantage to control the steering of the medical device.

As described herein, the control system may steer an endoscope; however, it will be understood that the control system may also be employed to steer other medical devices such as instruments containing end-effectors, including scissors, forceps, lithotripters, snares, or the like.

Various structural and functional features of the control system will be described below. It will be understood that the control system may be located in the handle of a medical device, placed external to the patient's body. Those skilled in the art will appreciate that the control system may be located in other portions of the medical device without departing from the scope of the present disclosure.

Figure 1:
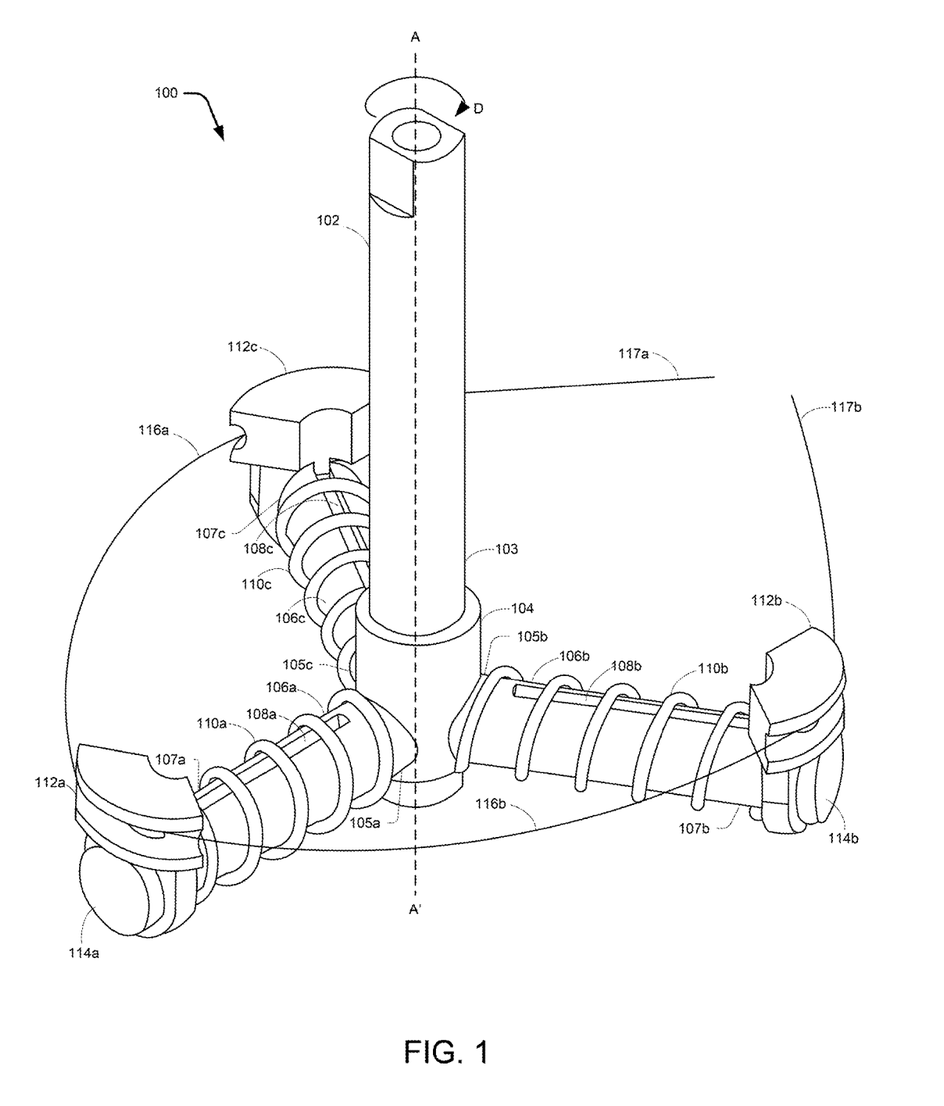
FIG. 1 is a partial isometric view of an exemplary control system according to an embodiment.

According to an embodiment, a control system 100 is shown in a partial isometric view in FIG. 1. The system 100 may be configured to control a medical device (not shown), such as an endoscope, having a deflectable distal region. The system 100 may be located in a proximal portion, such as a handle, of the endoscope.

The terms "proximal" and "distal" are used herein to refer to the relative positions of the components of the exemplary system 100. When used herein, "proximal" refers to a position relatively closer to the surgeon using the system 100. In contrast, "distal" refers to a position relatively further away from the surgeon using the system 100 or closer to a surgical site located within the patient's body.

The system 100 may include a shaft 102 and an attachment member 104 operably coupled to the shaft 102. The attachment between the shaft 102 and the attachment member 104 may be either temporary or permanent. The attachment may be achieved by any suitable means known in the art, including, e.g., by snap-fit or by threaded engagement between the attachment member 104 and the shaft 102. Other methods such as, e.g., soldering, brazing, or the like may also be used.

The shaft 102 may include an elongate structure. The shaft 102 may be cylindrical (e.g., with a circular cross-section). Alternatively, other suitable cross-sections such as, but not limited to, rectangular, triangular, oval, irregular, or the like may also be contemplated. The cross-sectional configuration of the shaft 102 may be uniform or may vary along its length. The shaft 102 may be tubular or solid. The shaft 102 and/or the attachment member 104 may be made of any of a variety of materials suitable to transmit an applied force from the shaft 102 to the attachment member 104. For example, such materials may be rigid or a semi-rigid. Examples may include metals, polymers, alloys, or the like. For instance, the material may include stainless steel, nitinol, or the like.

The shaft 102 may include a knob (not shown) that may be gripped by the user to rotate the shaft 102. Alternatively, another device may be provided to rotate the shaft 102, e.g., a lever or the like, which may be rotated by the user or a drive mechanism (e.g., a motor). The shaft 102 may be configured to rotate about a longitudinal axis A-A'. The rotation of the shaft 102 may cause the rotation of the attachment member 104 in the same direction as the shaft 102. For example, turning the shaft 102 in a clockwise direction may cause rotation of the attachment member 104 in a clockwise direction, and turning the shaft 102 in a counter-clockwise direction may cause rotation of the attachment member 104 in a counter-clockwise direction.

One or more arms 106a, 106b, and 106c (collectively, arms 106) may be attached to the attachment member 104 and may extend radially outwards therefrom. Each arm 106 may include an inward end 105a, 105b, and 105c (collectively, inward ends 105) and an outward end 107a, 107b, and 107c (collectively, outward ends 107). In the embodiment shown in FIG. 1, the radially-extending arms 106 may be located in a plane that is perpendicular to a plane extending along the longitudinal axis A-A'. This is merely an example and should not be understood as limiting other orientations of the arms 106.

In the embodiment shown in FIG. 1, the arms 106 may be tubular and may have a circular cross-section. Other cross-sections such as rectangular, triangular, oval, irregular, or the like may also be contemplated. The arms 106 may be securely attached to the attachment member 104 either permanently or temporarily. Exemplary means of attachment may include threading, gluing, snap fitting, soldering or brazing. Those skilled in the art will appreciate that other suitable attachment means may also be contemplated. Alternatively, the arms 106 may be formed integrally with the attachment member 104.

The location of the arms 106 as described above and shown in the figures is only for the purpose of illustration. Other locations may be used. Further details of arms 106 will be provided with reference to FIGS. 4-7 below.

The system 100 may further include arm slots 108a, 108b, and 108c (collectively, arm slots 108) on an outer surface of the respective arms 106. The arm slots 108 may be configured to extend at least partially between the inward ends 105 and the outward ends 107 of the respective arms 106. Alternatively, the respective arm slots 108 may be configured to run along the entire length of the arms 106.

The system 100 may also include one or more pulley pieces 112a, 112b, 112c (collectively, pulley pieces 112) slidably mounted on the respective arms 106. Each pulley piece 112 may include a projection 122 (FIGS. 2-5) configured to engage the respective arm slots 108. In the embodiment shown in FIG. 1, three pulley pieces 112 and three arms 106 are provided, but it is understood that any number of pulley pieces 112 and arms 106 greater than or less than three may be provided.

The pulley pieces 112 may be configured to engage a first control element 116a and a second control element 116b (collectively, control elements 116). The control elements 116 may each include a distal end 117a and 117b that is attached near a distal end of a medical device, such as an endoscope (not shown). The control elements 116 may include one or more wires (e.g., a braided wire, multiple wires, etc.), cables, ribbons, or other similar elongate structure. Those skilled in the art will appreciate that any suitable control elements may also be contemplated. In an embodiment, the first and second control elements 116a and 116b (e.g., the proximal ends thereof) may be connected separately to the same pulley piece (e.g., pulley piece 112a) as shown in FIG. 1, or to different pulley pieces. Alternatively, the first and second control elements 116a and 116b may be connected together (e.g., at the proximal ends of the control elements) or integrally formed as a single control element (e.g., a single wire), which may be connected to the same pulley piece (e.g., pulley piece 112a).

As noted above, the pulley pieces 112 may slide inwardly and outwardly on the arms 106 via engagement of the projections 122 in the respective arm slots 108. The outward movement of the pulley pieces 112 may be limited using a cap member 114a, 114b, and 114c (collectively, cap members 114) attached to the respective arms 106a, 106b, 106c. Each cap member 114 may be configured and dimensioned to prevent the pulley pieces 112 from sliding off the outward ends 107 of the arms 106. The arms 106, the pulley pieces 112, and/or the cap members 114 may be made of any of a variety of materials, such as metals, polymers, alloys, or the like. For instance, the material may include molded plastic.

The system 100 may also include resilient or biasing members, such as springs 110a, 110b, and 110c (collectively, springs 110), located between the respective pulley pieces 112 and the attachment member 104. The springs 110 may be formed of steel (e.g., steel wire) or other material known in the art for forming springs. Details of the springs 110, pulley pieces 112, cap members 114, and control elements 116 will be described below with reference to FIGS. 2-7.

Figure 2:
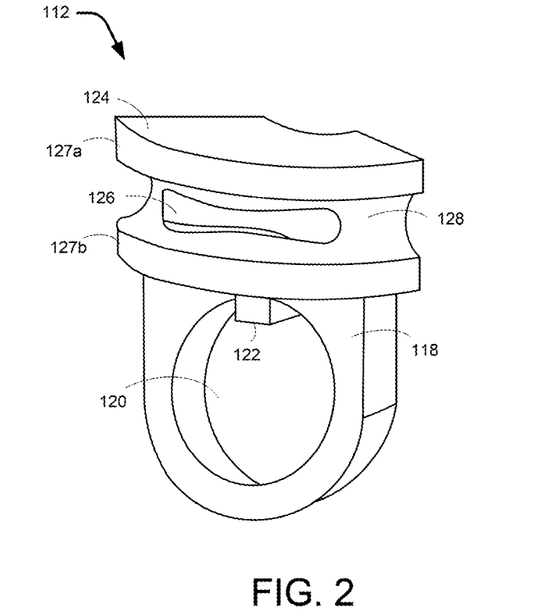
FIG. 2 is a detailed view of a pulley piece according to an embodiment.
Figure 5:
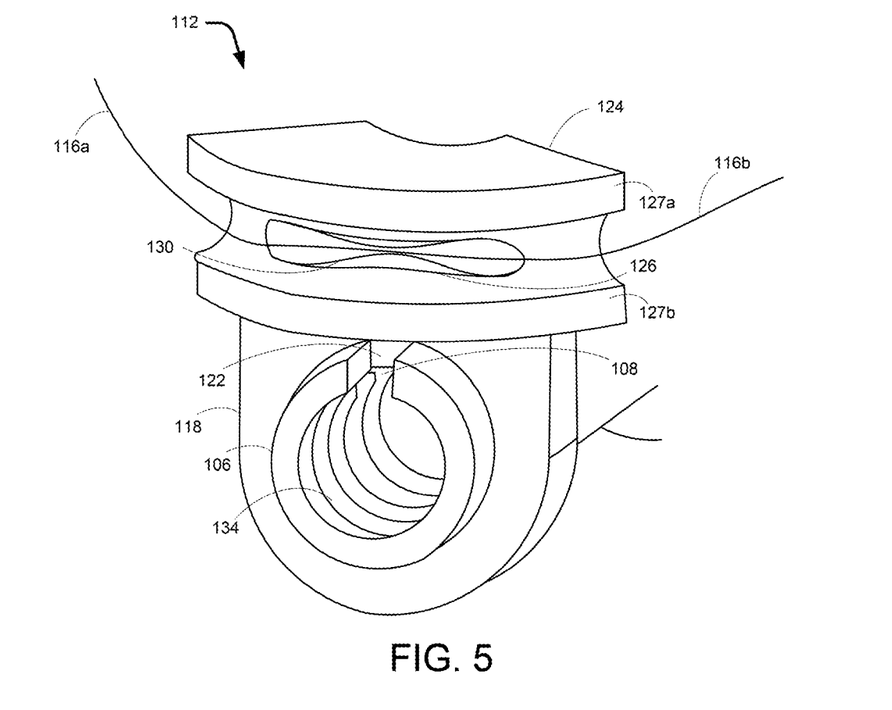
FIG. 5 depicts the attachment of the pulley piece of FIG. 2 to the arm of FIG. 4 according to an embodiment.

FIG. 2 is a detailed view showing features of the pulley piece 112, in accordance with an embodiment of the present disclosure. As shown, the pulley piece 112 may include a pulley bracket 118 having an opening configured and dimensioned to slidably receive and engage the arm 106. In the embodiment shown in FIG. 2, the pulley bracket 118 may include an axial bore 120 defining the opening. The axial bore 120 may be dimensioned to be mounted over the arm 106, as shown in FIG. 5.

The projection 122 that is slidably engaged with and securely received in the arm slot 108 may be disposed radially inwardly from the axial bore 120. As shown, the projection 122 may have a rectangular-shaped configuration, however, other configurations such as, square, polygonal, irregular, or the like may also be contemplated. Once engaged within the longitudinal arm slot 108, the projection 122 may allow the pulley piece 112 to move longitudinally (lengthwise) inwardly and outwardly in relation to the arm 106, while preventing rotation of the pulley piece 112 about the arm 106.

Figure 3:
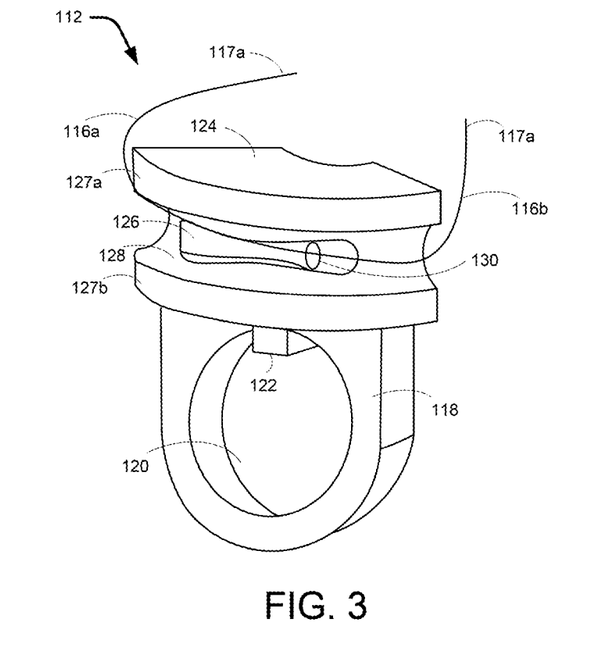
FIG. 3 is a detailed view of the pulley piece of FIG. 2 connected to control elements according to an embodiment.

The pulley piece 112 may also include a pulley head 124, which may have a semi-circular profile and which may connect to the pulley bracket 118. The pulley head 124 may include an outer surface configured to engage one or more of the control elements 116a and/or 116b. As shown in FIG. 3, the pulley head 124 may engage both of the control elements 116a and 116b.

In the example shown, the pulley head 124 may include a control element engaging surface, such as a groove 128 defined by flanges 127a and 127b (collectively, flanges 127) on the peripheral surface of the pulley head 124. The groove 128 in the pulley head 124 may further include a crimp slot 126. In particular, the groove 128 may guide and/or receive the control elements 116a and 116b that are at least partially wound around the pulley piece 112.

Referring now to FIG. 3, the proximal ends of the control elements 116a and 116b may be connected to the pulley piece 112 (e.g., pulley piece 112a of FIG. 1). As shown, a crimp tube 130 may be employed to stabilize the proximal ends of the control elements 116, while being attached to the pulley piece 112. The crimp tube 130 may include a circular cross-section. Other suitable cross-sections such as, but not limited to, rectangular, triangular, irregular, oval, or the like may also be contemplated. The crimp tube 130 may be made up of any suitable material such as, but not limited to, metals, polymers, alloys, or the like. Exemplary materials may include, but not limited to, stainless steel or nitinol.

The proximal ends of the control elements 116 may be secured inside the crimp tube 130 such that squeezing the crimp tube 130 may hold the proximal ends of the respective elements 116 inside the crimp tube 130. Further, when holding the two control elements 116, the crimp tube 130 may slide into the crimp slot 126 of the pulley piece 112. In some embodiments, the crimp tube 130 may be frictionally fitted within and/or snapped into the crimp slot 126. Alternatively, the crimp tube 130 may be glued or threaded into the crimp slot 126. As those skilled in the art may appreciate, various methods may be used to releasably or permanently secure the crimp tube 130 within the crimp slot 126.

In the embodiment shown in FIG. 1, after securing the control elements 116a and 116b to the same pulley piece 112a, the control elements 116 may be wrapped around the other pulley pieces 112. For example, the control element 116a may be wrapped around pulley piece 112c (e.g., within the groove 128 of the pulley piece 112c), and the control element 116c may be wrapped around pulley piece 112b (e.g., within the groove 128 of the pulley piece 112b). In another embodiment, one or more of the control elements 116 may be additionally wrapped around the grooves 128 of all of the pulley pieces 112 prior to operation of the system 100. For example, one or both of the control elements 116a and 116b may wrap around all three pulley pieces 112a, 112b, and 112c.

Further, instead of crimping, the control elements 116 may be attached using other methods to the respective pulley piece(s) 112. For example, in an embodiment, the proximal ends of the control elements 116 may be attached via a pivotal connection (e.g., a pivot pin) to the pulley piece 112a. The pivotal connection may assist in reducing kinking in certain instances.

Figure 4:
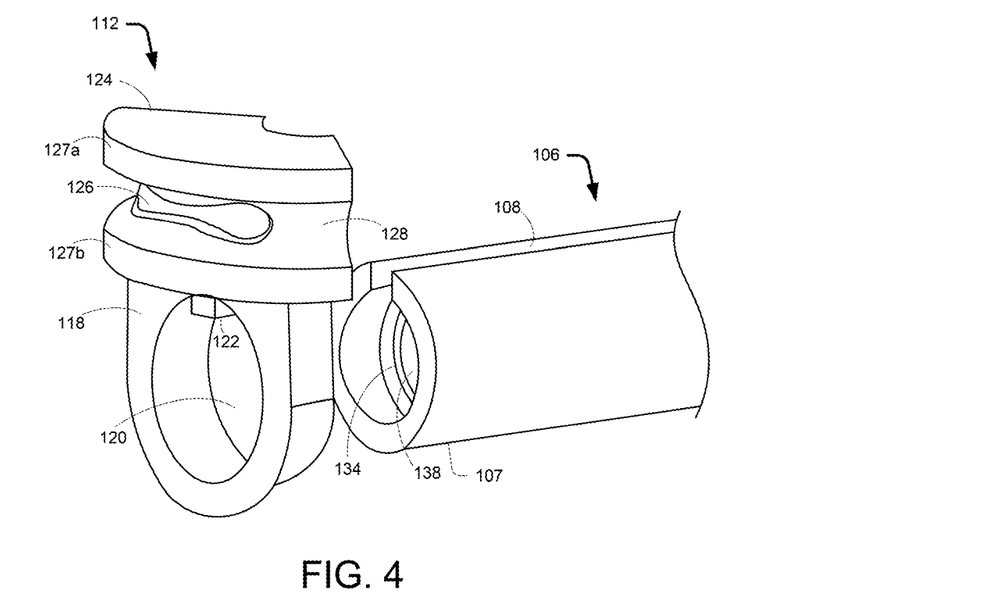
FIG. 4 is a partial isometric view of the pulley piece of FIG. 2 and an arm according to an embodiment.

Each pulley piece 112 may be oriented relative to the corresponding arm 106 such that the projection 122 on the pulley bracket 118 may be received within the longitudinal arm slot 108 on the arm 106, as shown in FIGS. 4 and 5. Furthermore, as depicted in FIG. 5, the outward end 107 of the arm 106 may include a bore 134 configured to receive at least a portion of the respective cap member 114.

Figure 6:
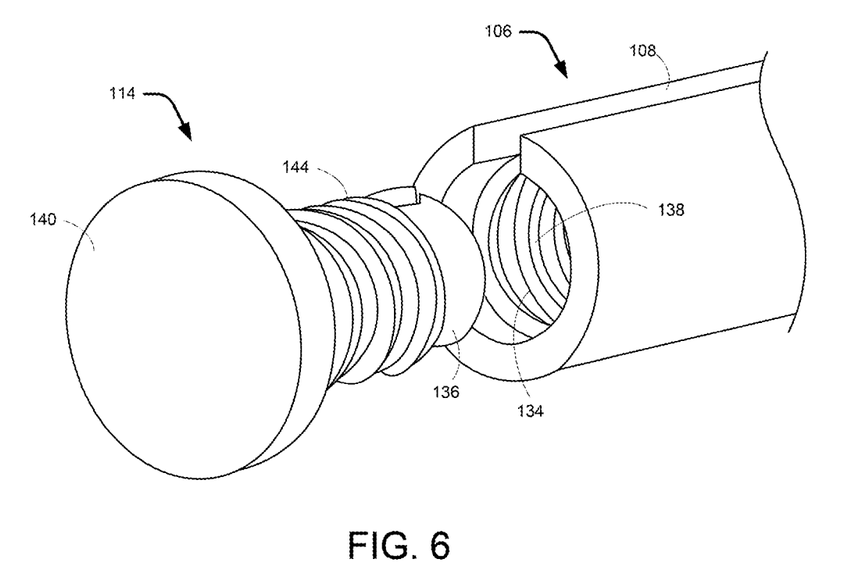
FIG. 6 is a partial isometric view of a cap member and an arm according to an embodiment.

FIG. 6 depicts the cap member 114 configured to engage with the arm 106. As described above, the cap member 114 may securely retain the pulley piece 112 within the arm slot 108. In particular, the cap member 114 may be dimensioned to retain the pulley piece 112 within the arm slot 108. In the embodiment shown, the cap member 114 may include a proximal circular portion 140 attached to a shaft portion 142. The shaft portion 142 may include external male threads 144 on its outer surface, and the male threads 144 may be configured to engage with internal female threads 138 inside the arm 106 to secure the arm 106 and the cap member 114 together. Other suitable methods for securing the cap member 114 to the outward end 107 of the arm 106 may include a snap-fit, a leur-lock, gluing, or the like.

Figure 7:
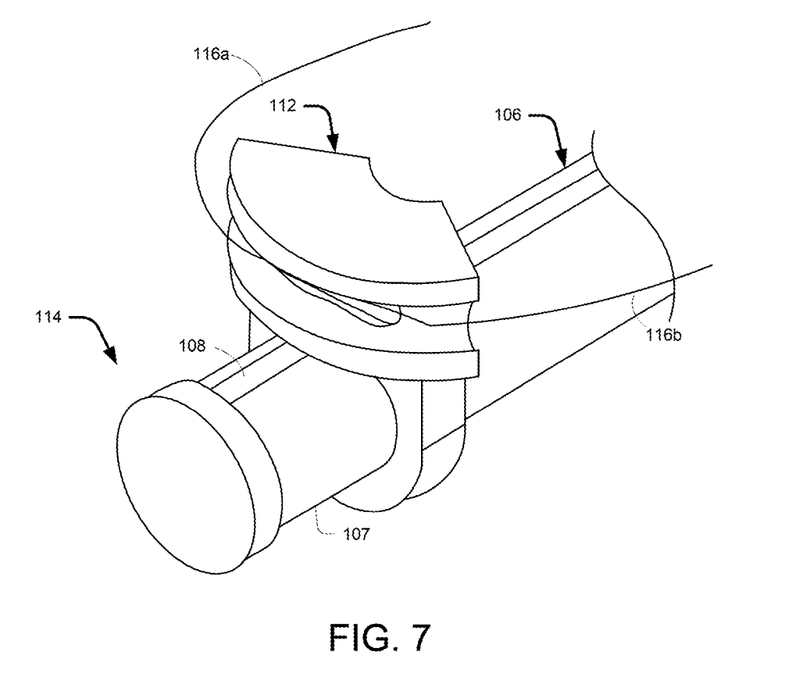
FIG. 7 is a partial isometric view of a pulley piece, control elements, an arm, and a cap member connected together according to an embodiment.

In addition, the cap member 114 may be configured to keep the pulley piece 112 engaged within the arm 106, as shown in FIG. 7. As shown, once the pulley piece 112 is engaged on the arm 106, the circular portion 140 of the cap member 114 has an outer diameter that is large enough to limit outward movement of the projection 122 in the longitudinal arm slot 108. Thus, the cap member 114 may help to keep the pulley piece 112 slidably attached to the arm 106.

Also, as described above, each spring 110 may be located between the corresponding pulley piece 112 and the attachment member 104, and may be configured to urge the pulley piece 112 in an outward direction along the arm 106. As shown, the spring 110 may be wrapped around an outer surface of at least a portion of length of the corresponding arm 106. In an embodiment, the spring 110 may be attached at one end to the corresponding pulley piece 112 and attached at the other end to the attachment member 104.

Figure 8:
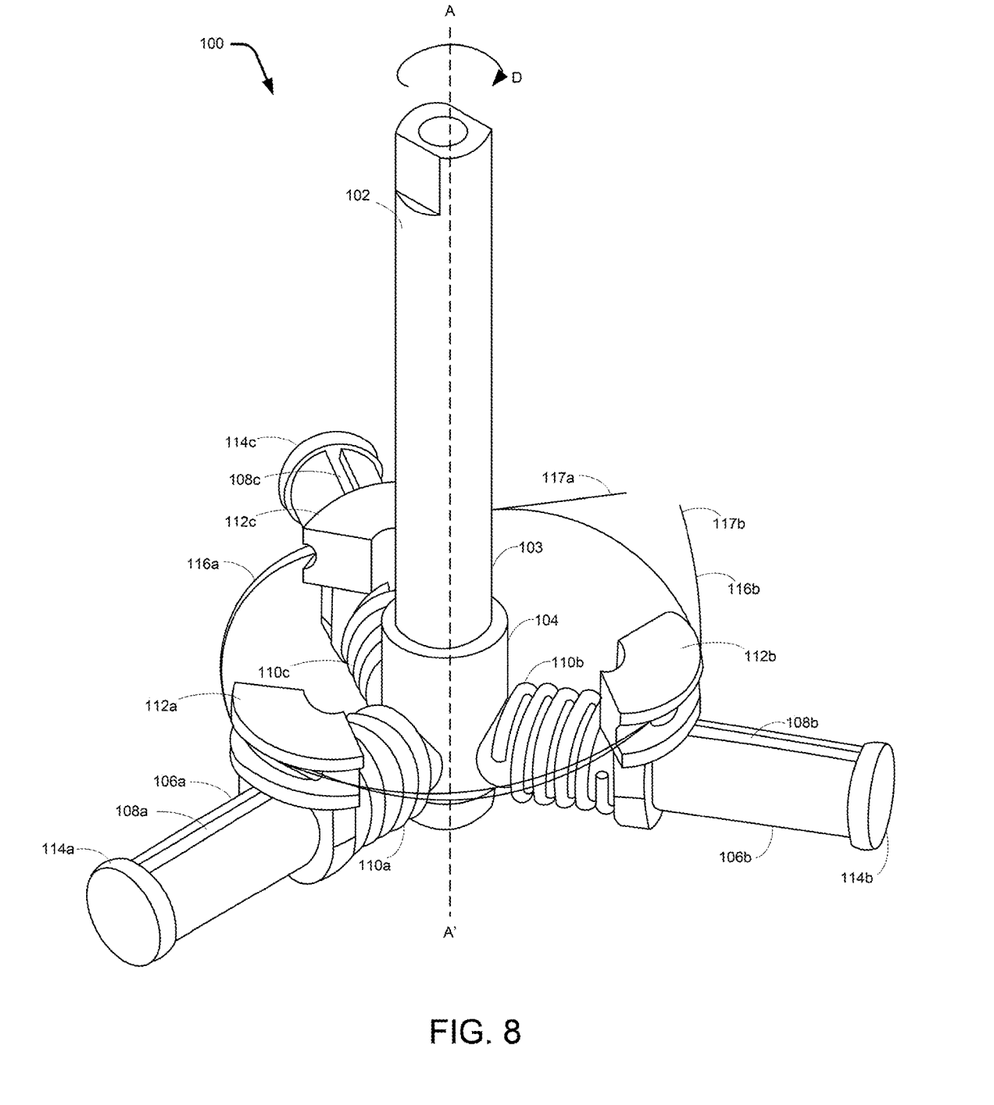
FIG. 8 illustrates the system of FIG. 1 during use according to an embodiment.

The control system 100 may be operated by turning the shaft 102 in a direction (clockwise in the direction D or counterclockwise) to pull one of the control elements 116a or 116b. As the shaft 102 is turned, one of the control elements 116 may be pulled while the other control element 116 is released and the control elements 116 may wrap around the grooves 128 of the pulley pieces 112. In an embodiment, the shaft 102 (and therefore also the attachment member 104 and the pulley formed by the pulley pieces 112) may rotate less than 180 degrees to achieve the desired deflection. Alternatively, the components may rotate greater than or equal to 180 degrees to achieve the desired deflection. As the shaft 102 is turned, the forces acting on the pulley pieces 112 by the control elements 116 may increase so that the control elements 116 may cause one or more of the pulley pieces 112 to slide inward against the outward urging force of the springs 110.

For example, in the illustrated embodiment, the shaft 102 may be rotated in a clockwise direction D so that the attachment member 104 may rotate in direction D. This may also rotate the pulley pieces 112 attached thereon, pulling the second control element 116b, while releasing the first control element 116a. As the pulley pieces 112 are rotated, the pulled second control element 116b may elongate and also experience an increase in normal strain and normal stress, and consequently the force opposing the rotation of the pulley pieces 112 may be increased. Under the normal conditions, the normal strain on the second control element 116b may be predominantly axial, thus the cross-sectional area of the second control element 116b may be constant. As a result, the increase in normal strain in the second control element 116b may result in an increase in the force opposing the pulley pieces 112 and the springs 110. This opposing force on the pulley pieces 112 may compress the springs 110, moving the springs 110 towards the shaft 102. As shown, the two control elements 116a and 116b may be wound against the three pulley pieces 112. The pulley pieces 112 may move toward the shaft 102 and, where the pulley pieces 112 all move inwardly to generally the same extent, they may substantially define a circle. An "effective pulley diameter" may be defined by the average radius between the central axis A-A' and the grooves 128 of the pulley pieces 112. As the springs 110 are compressed, the effective pulley diameter may decrease.

The gear ratio may increase as the effective pulley diameter decreases. For example, in the illustrated embodiment, the increased gear ratio may result from an increase in the ratio of the diameter of the knob (or other device that is rotated to cause the rotation of the shaft 102) and the effective pulley diameter. This may provide a mechanical advantage to the system 100 by providing increased torque on the pulley pieces 112 for relatively lower force on the shaft 102. In particular, the pulley pieces 112 may form a variable-diameter, collapsible pulley that allows for a reduction in torque for producing a desired deflection based on a certain rotation of the knob (or other device that is rotated to cause the rotation of the shaft 102) compared to a fixed-diameter pulley.

Thus, the system 100 described above may provide a mechanical advantage for steering endoscopes that may not be provided by conventional endoscopes that employ a pulley stack for deflection of the distal end. Such conventional designs may require a larger amount of force to rotate the pulley stack, and the amount of force required to rotate the pulley stack may increase as the degrees of rotation increases.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A method for steering a distal end of a medical device, comprising:
rotating a shaft of a control system about a longitudinal axis to cause movement of a control element and deflection of the distal end of the medical device, wherein:
the control element extends from the control system to the distal end of the medical device, and
the control system includes (1) a plurality of arms and (2) a collapsible pulley having a variable diameter, wherein the collapsible pulley includes a plurality of pulley pieces, and each of the plurality of pulley pieces is movably mounted to a corresponding one of the plurality of arms; and
decreasing the diameter of the pulley.

2. The method of claim 1, wherein decreasing the diameter of the pulley includes moving at least one of the plurality of pulley pieces towards the shaft along the corresponding one of the plurality of arms.

3. The method of claim 1, wherein the plurality of arms extend radially outward from the shaft.

4. The method of claim 1, wherein rotating the shaft causes decreasing the diameter of the pulley.

5. The method of claim 1, wherein the control system further includes at least one biasing member located between the shaft and the collapsible pulley.

6. The method of claim 1, wherein the collapsible pulley includes at least three pulley pieces, and decreasing the diameter of the collapsible pulley includes moving at least one of the pulley pieces radially inward towards the shaft.

7. A method for steering a distal end of a medical device, comprising:
  rotating a shaft of a control system, wherein the control system includes an elongated shaft, a plurality of arms extending from the shaft, and a plurality of pulley pieces;
  moving at least one pulley piece of the plurality of pulley pieces along one of the plurality of arms towards the shaft, wherein the at least one pulley piece is a first pulley piece, and the one of the plurality of arms is a first arm;
  moving a second pulley piece of the plurality of pulley pieces along a second arm of the plurality of arms towards the shaft;
  moving a third pulley piece of the plurality of pulley pieces along a third arm of the plurality of arms towards the shaft; and
  deflecting a distal end of the medical device.

8. The method of claim 7, wherein a control element extends from the at least one pulley piece to the distal end of the medical device, and rotating the shaft causes movement of the control element to deflect the distal end of the medical device.

9. The method of claim 8, wherein the control element is releasably coupled to the at least one pulley piece.

10. The method of claim 7, further comprising a biasing member located between the shaft and the at least one pulley piece.

11. The method of claim 7, wherein rotating the shaft causes moving the at least one pulley piece and deflecting the distal end.

12. The method of claim 7, wherein:
  the one of the plurality of arms includes an arm slot extending at least partially along an outer surface of the one of the plurality of arms; and
  the at least one pulley piece includes a projection slidably received within the arm slot.

13. A method for steering a distal end of a medical device, comprising:
  rotating a shaft of a control system about a longitudinal axis to rotate a collapsible pulley formed from a plurality of pulley pieces, each pulley piece of the plurality of pulley pieces being mounted on a corresponding one of a plurality of arms;
  sliding at least one of the pulley pieces along the corresponding one of the plurality of arms, wherein each arm includes an inward end positioned near the shaft and an outward end positioned away from the shaft;
  compressing at least one biasing member located between the inward end and the outward end of the one of the plurality of arms; and
  tensioning at least one control element releasably coupled to at least one of the plurality of pulley pieces.

14. The method of claim 13, wherein:
  the plurality of pulley pieces includes at least three pulley pieces slidably mounted on the corresponding arms and forming an effective pulley diameter; and
  as the shaft is rotated, the effective pulley diameter decreases.

15. The method of claim 14, wherein, as the shaft is rotated, a gear ratio increases, the gear ratio being a ratio between a diameter of a device that is rotated to cause the rotation of the shaft and the effective diameter of the pulley.

16. The method of claim 13, further comprising deflecting the distal end of the medical device.

17. The method of claim 16, wherein the medical device is an endoscope.

18. The method of claim 13, wherein the at least one control element is fixed to the distal end of the medical device, such that tensioning the at least one control element causes deflection of the distal end of the medical device.

* * * * *